(12) United States Patent
Clark (10) Patent No.: US 11,868,535 B2
(45) Date of Patent: Jan. 9, 2024

(54) WEARABLE DEVICE THAT PROVIDES SPACED RETRIEVAL ALERTS TO ASSIST THE WEARER TO REMEMBER DESIRED INFORMATION

(71) Applicant: Memory On Hand Inc., Calgary (CA)

(72) Inventor: Cameron Mackenzie Clark, Calgary (CA)

(73) Assignee: Memory On Hand Inc., Calgary (CA)

( * ) Notice: Subject to any disclaimer, the term of this patent is extended or adjusted under 35 U.S.C. 154(b) by 0 days.

(21) Appl. No.: 17/903,590

(22) Filed: Sep. 6, 2022

(65) Prior Publication Data

US 2023/0082625 A1    Mar. 16, 2023

(30) Foreign Application Priority Data

Sep. 16, 2021 (CA) .................................. CA 3130972

(51) Int. Cl.
*G06F 3/048* (2013.01)
*G06F 3/01* (2006.01)
(Continued)

(52) U.S. Cl.
CPC .............. *G06F 3/016* (2013.01); *G06F 1/163* (2013.01); *G08B 6/00* (2013.01); *G08B 21/24* (2013.01)

(58) Field of Classification Search
CPC  G06F 3/016; G06F 1/163; G08B 6/00; G08B 21/24
See application file for complete search history.

(56) References Cited

U.S. PATENT DOCUMENTS 10,181,251 B2   1/2019  Gao
10,257,335 B2   4/2019  Chiu
(Continued)

FOREIGN PATENT DOCUMENTS

AU    2004248605 B2    12/2004
CN     105193384 A      8/2015
(Continued)

OTHER PUBLICATIONS

Kim, A. S., Wong-Kee-You, A. M., Wiseheart, M., & Rosenbaum, R. S. (2019). The spacing effect stands up to big data. Behavior Research Methods, 51(4), 1485-1497. https://doi.org/10.3758/s13428-018-1184-7.

(Continued)

*Primary Examiner* — David Phantana-angkool
(74) *Attorney, Agent, or Firm* — ATMAC Patent Services Ltd.; Andrew T. MacMillan (57) ABSTRACT

A wearable device to assist with memory that includes a processor, a haptic output device, and a button. When a wearer of the device encounters a piece of information they want to remember but thinks they may forget (e.g. the name of someone they just met; a phone number; a coupon code; an address; a new word definition, etc.) they simply press the single button on the device. The single button press initiates a pre-set schedule of tactile reminders about that piece of information. The reminders are vibrational and/or haptic outputs triggered by the processor that come quickly at first, and then become more spaced out over time. The device beneficially assists users in implementing the empirically supported 'spaced retrieval' memory strategy—where spaced retrieval refers to a method of retrieving information at longer and longer intervals to aid memory retention for selected pieces of information.

20 Claims, 6 Drawing Sheets

(51) Int. Cl.
*G06F 1/16* (2006.01)
*G08B 6/00* (2006.01)
*G08B 21/24* (2006.01)

(56) References Cited

U.S. PATENT DOCUMENTS

| | | | |
|---|---|---|---|
| 11,321,677 B1 * | 5/2022 | Newman | G08B 21/24 |
| 11,669,235 B2 * | 6/2023 | Crowley | G08B 5/22 |
| | | | 715/771 |
| 2005/0272408 A1 | 12/2005 | Wilkes-Gibbs et al. | |
| 2011/0224505 A1 | 9/2011 | Sadhu | |
| 2012/0251989 A1 | 10/2012 | Wetmore et al. | |
| 2013/0110009 A1 | 5/2013 | Salorio | |
| 2016/0239933 A1 | 8/2016 | Yang et al. | |
| 2017/0053542 A1 * | 2/2017 | Wilson | G09B 5/02 |
| 2017/0323057 A1 | 11/2017 | Karvela et al. | |
| 2019/0265796 A1 * | 8/2019 | Levesque | G06F 3/016 |
| 2019/0302853 A1 | 10/2019 | Stewart | |
| 2019/0325716 A1 * | 10/2019 | Khoshkava | G08B 6/00 |
| 2020/0333929 A1 * | 10/2020 | Bhullar | H04W 4/12 |
| 2020/0336585 A1 * | 10/2020 | Bhullar | G06F 3/0481 |
| 2021/0149346 A1 * | 5/2021 | Wright | G04G 9/0005 |
| 2021/0349617 A1 * | 11/2021 | Crowley | G06F 3/04883 |
| 2022/0155868 A1 * | 5/2022 | Musgrove | G06F 1/163 |
| 2023/0082625 A1 * | 3/2023 | Clark | G08B 6/00 |
| | | | 715/702 |
| 2023/0161470 A1 * | 5/2023 | Crowley | G06F 3/0482 |
| | | | 715/771 |

FOREIGN PATENT DOCUMENTS

| | | |
|---|---|---|
| CN | 105005380 A | 10/2015 |
| CN | 106781760 A | 1/2017 |
| CN | 109040462 A | 12/2018 |
| CN | 109088815 A | 12/2018 |
| CN | 110037715 A | 7/2019 |
| CN | 110138038 A | 8/2019 |
| CN | 111596765 A | 8/2020 |
| CN | 111599134 A | 8/2020 |
| JP | 6620374 B2 | 4/2017 |
| WO | 2015127143 A1 | 8/2015 |
| WO | 2015154440 A1 | 10/2015 |
| WO | 2015187510 A1 | 12/2015 |
| WO | 2017036516 A1 | 3/2017 |
| WO | 2018120863 A1 | 7/2018 |

OTHER PUBLICATIONS

Latimier, A., Peyre, H., & Ramus, F. (2020). A meta-analytic review of the benefit of spacing Out retrieval Practice episodes on retention. Educational Psychology Review. https://doi.org/10.1007/s10648-020-09572-8.

* cited by examiner

WEARABLE DEVICE THAT PROVIDES SPACED RETRIEVAL ALERTS TO ASSIST THE WEARER TO REMEMBER DESIRED INFORMATION

CROSS-REFERENCE TO RELATED APPLICATIONS

This application claims the benefit of priority of Canadian Patent Application No. 3,130,972 filed Sep. 16, 2021, which is incorporated herein by reference.

BACKGROUND OF THE INVENTION

(1) Field of the Invention

The invention pertains generally to tools to assist with memory. More specifically, the invention relates to a wearable device that provides haptic feedback to assist the wearer to remember desired information.

(2) Description of the Related Art

A general problem is that memory is a perishable skill, both normatively over the lifespan, but also certainly in response to neurological insult or injury like brain injury or neurodegenerative processes like Alzheimer's Disease. Some types of memory are impacted more than others during the aging process. For example, immediate memory and recent memory are impacted more than say remote memory. These changes start as early as our mid-20's, which means memory issues are a problem that affects a wide range of the population.

Both modern and ancient strategies exist to help us remember. Modern solutions include phone apps (e.g., notes, calendars, reminders etc.) and desktop computer programs (e.g., Anki, supermemo, etc.). Ancient strategies include things like writing important information down (e.g. names of new people), forming habits (e.g. to stop losing your keys), making associations (e.g. to remember where you parked), and practicing recall of important information.

The above solutions are effective in the right situations, but often let us down when we can't access them immediately when we encounter a piece of information we want to remember, but think or worry that we may forget. Consider remembering a difficult name of a person you were just introduced to—" . . . was it Miku, or Miko?". We absolutely could write this down on paper or jot it down in our phones mid-conversation, but we don't. Often the reason we don't is because it would be considered rude or embarrassing to do so right in the middle of a conversation. Thus, both the modern and ancient strategies are often not effective when and where we need it most—in day-to-day conversations or while out in the 'real world'.

Consequently, information that is desired to be remember is often lost, and this problem tends to get worse after the age of 55 or so.

BRIEF SUMMARY OF THE INVENTION

According to an exemplary embodiment of the invention there is disclosed a device that removes the tiny amounts of 'behavioural friction' between wanting to recall something, and actually doing something to help us recall it in the future.

According to an exemplary embodiment of the invention there is disclosed an instantly accessible wearable technology to assist users in implementing the empirically supported 'spaced retrieval' memory strategy—where spaced retrieval refers to a method of retrieving information at longer and longer intervals to aid memory retention for selected pieces of information.

According to an exemplary embodiment of the invention there is disclosed a wearable wrist-based tactile feedback device to augment memory consolidation and retrieval in everyday life.

According to an exemplary embodiment of the invention there is disclosed a single button device that allows wearers to essentially 'push' personally meaningful/important information from the present into their future. The implications are ostensibly few. People remember a phone number, name, or address that they may have forgotten. However, the impact of these 'memory successes' for healthy aging seniors that are worried about memory decline are huge. Increased confidence in memory and fewer memory mistakes have important implications for mood, prevention of cognitive decline and dementia, as well as less unnecessary healthcare utilization.

According to an exemplary embodiment, a wearable device to assist with memory includes a processor, a haptic output device, and a button. When a wearer of the device encounters a piece of information they want to remember but thinks they may forget (e.g. the name of someone they just met; a phone number; a coupon code; an address; a new word definition, etc.) they simply press the single button on the device. The single button press initiates a pre-set schedule of haptic reminders about that piece of information. The reminders are haptic outputs triggered by the processor that come quickly at first, and then become more spaced out over time. The device beneficially assists users in implementing the empirically supported 'spaced retrieval' memory strategy—where spaced retrieval refers to a method of retrieving information at longer and longer intervals to aid memory retention for selected pieces of information.

According to an exemplary embodiment, there is disclosed a non-transitory processor-readable medium comprising processor executable instructions that when executed by one or more processors cause the one or more processors to perform steps as shown and described herein.

These and other advantages and embodiments of the present invention will no doubt become apparent to those of ordinary skill in the art after reading the following detailed description of preferred embodiments illustrated in the various figures and drawings.

BRIEF DESCRIPTION OF THE DRAWINGS

The invention will be described in greater detail with reference to the accompanying drawings which represent preferred embodiments thereof.

DETAILED DESCRIPTION

Figure 1:
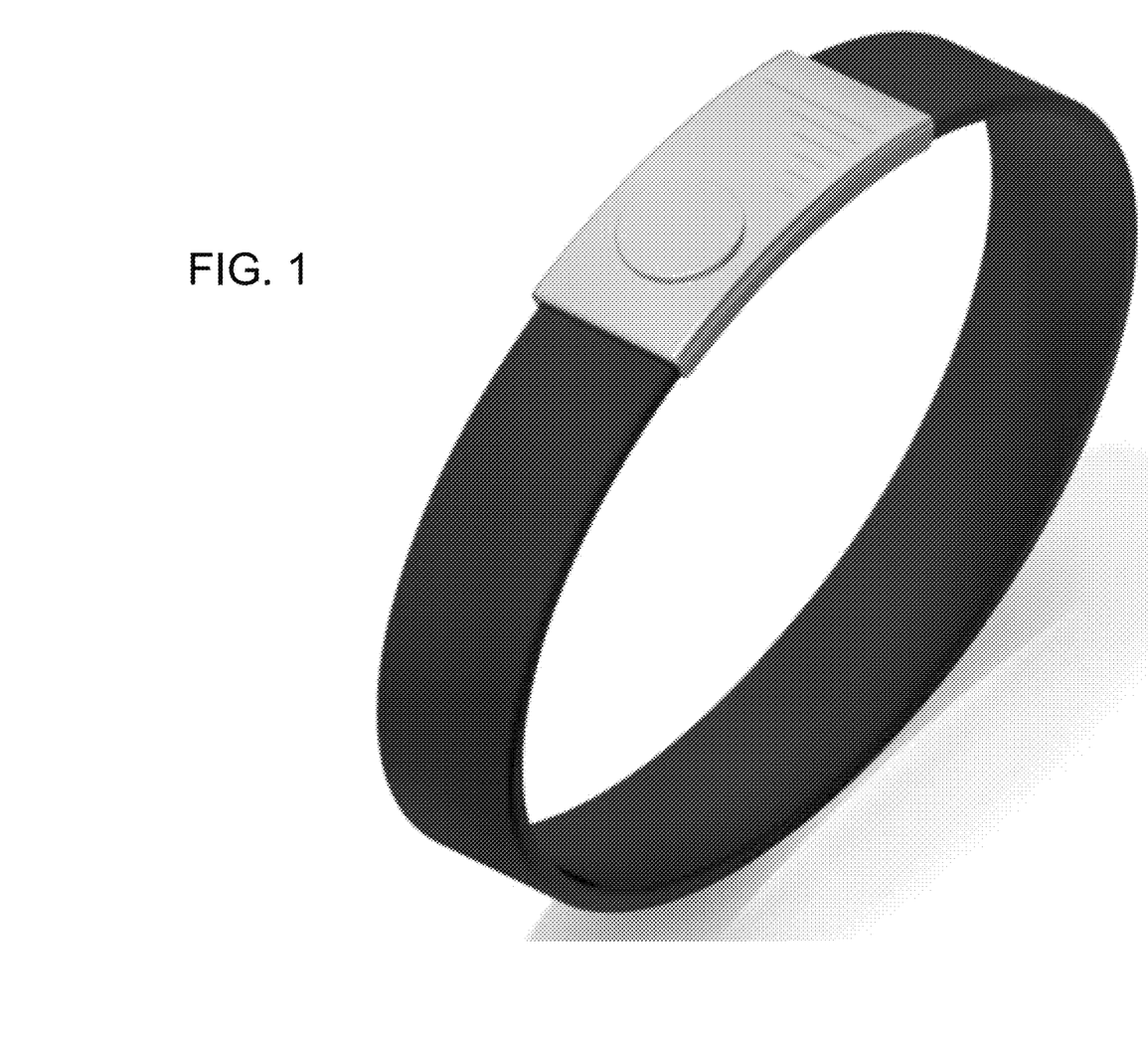
FIG. 1 illustrates a perspective view of a wearable memory assistance device that provides spaced retrieval alerts to assist the wearer to remember desired information according to an exemplary embodiment.
Figure 2:
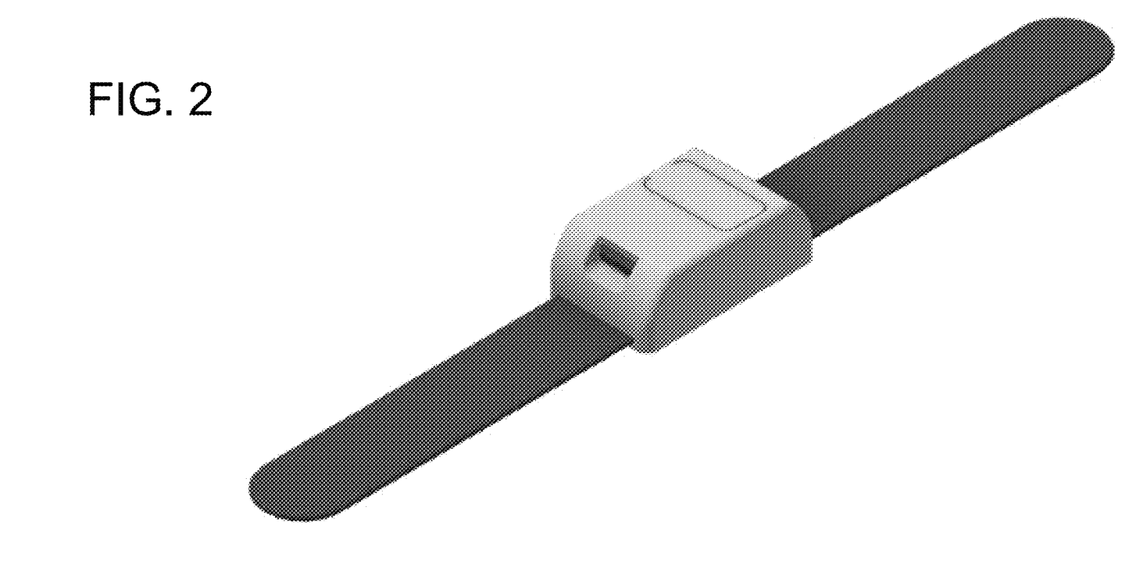
FIG. 2 illustrates a perspective view of another wearable memory assistance device according to an exemplary embodiment.
Figure 3:
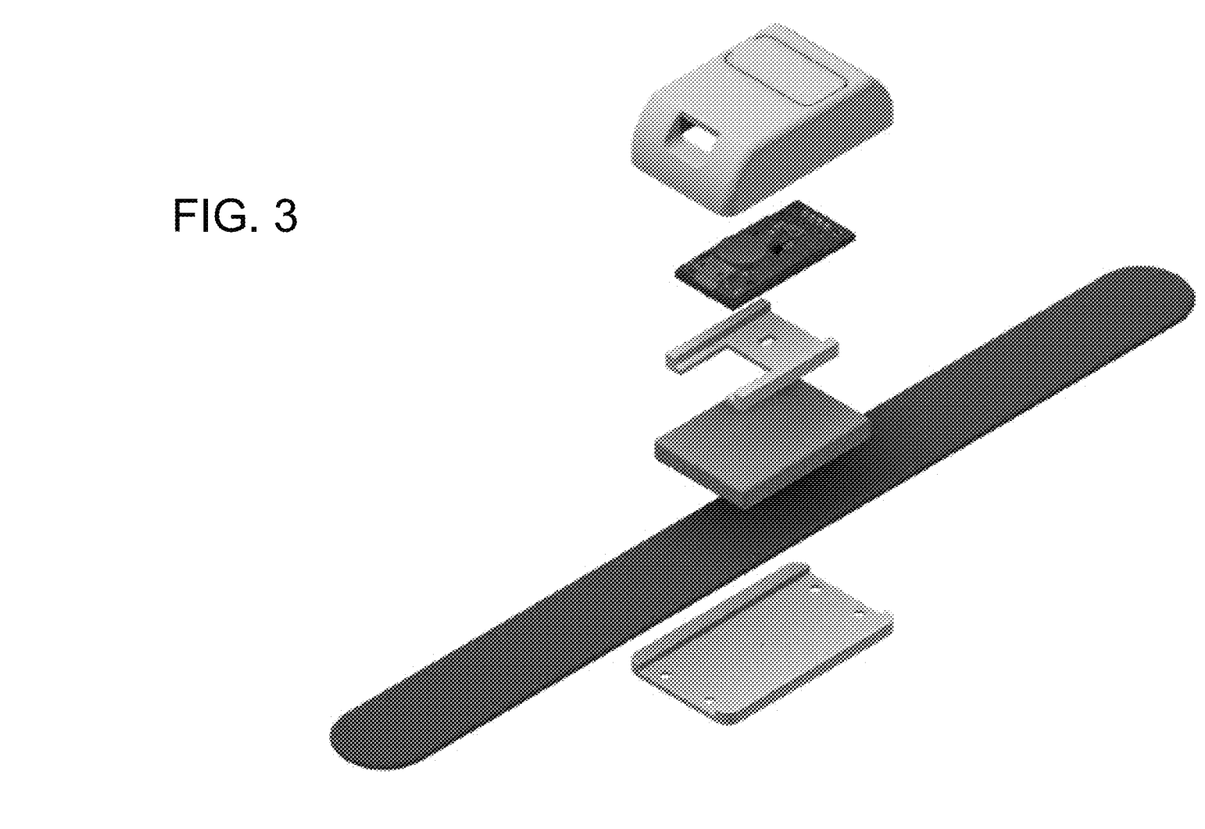
FIG. 3 illustrates an exploded perspective view of the wearable memory assistance device of FIG. 2 according to an exemplary embodiment.

FIGS. 1-3 illustrate various perspective views and exploded perspective view of a wearable device that provides spaced retrieval alerts to assist the wearer to remember desired information according to exemplary embodiments. The device in these embodiments is a very simple wrist-based (i.e. watch-like) tactile device intended to augment everyday memory in real world situations. The device includes a standard silicone bracelet wrist band supporting an electronic circuit board that includes a single button.

Figure 4:
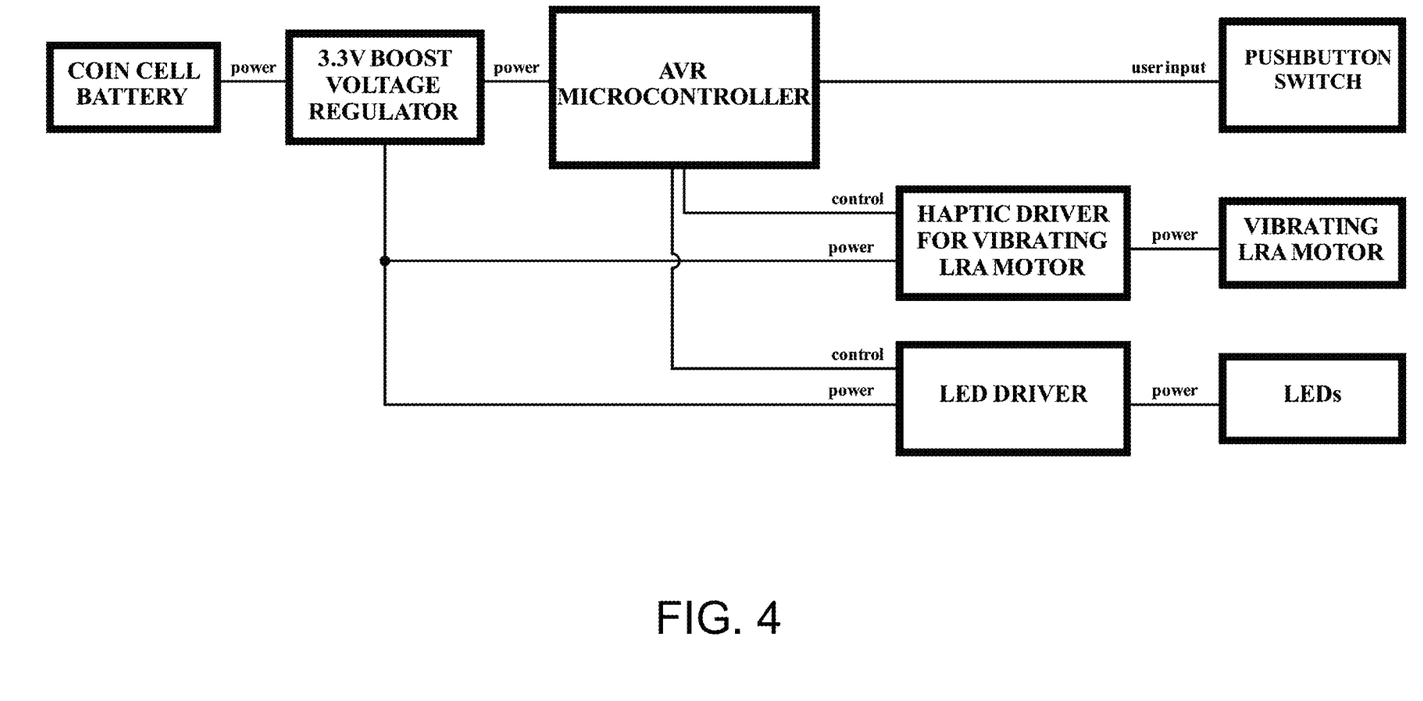
FIG. 4 illustrates a block diagram of the components of the electronic circuit of the wearable memory assistance device of FIG. 1.

FIG. 4 illustrates a block diagram of the components of the circuit board of the wearable device of FIG. 1. As illustrated, the electronic components include a battery, a voltage booster and regulator, a microcontroller, a pushbutton switch, a haptic driver, a vibrating motor, an LED driver, and a plurality of LEDs.

In short, the device is a single-button circuit board including a vibration motor and battery module attached to a standard silicone bracelet.

Figure 5:
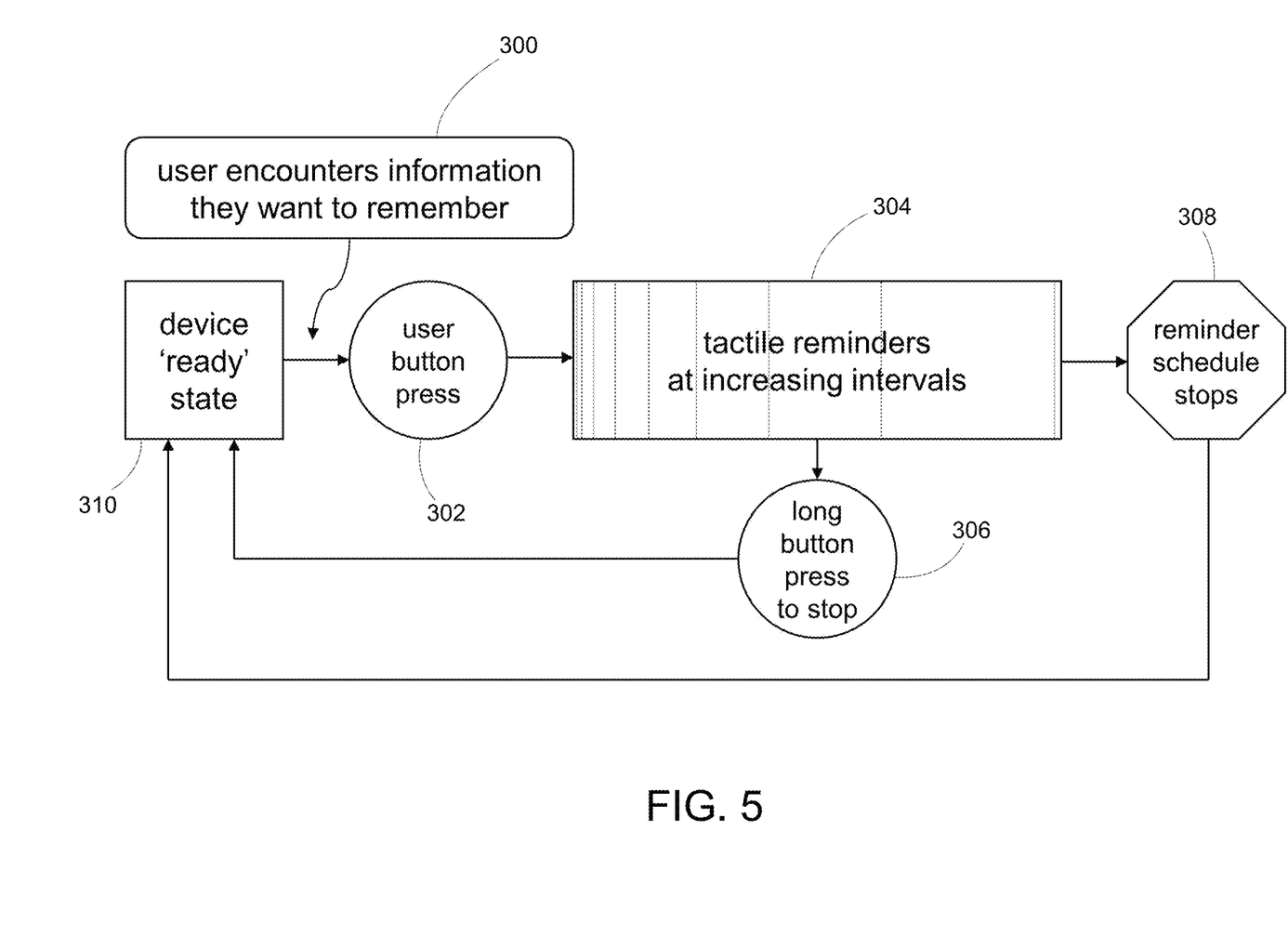
FIG. 5 illustrates a flowchart of operations of the wearable memory assistance device of FIGS. 1 and 2 to assist with memory according to an exemplary embodiment.

FIG. 5 illustrates a flowchart of operations of the wearable device disclosed above to assist with memory according to an exemplary embodiment. The steps of FIG. 5 may be performed by a user of the device in conjunction with one or more processors of the microcontroller. The steps of the flowchart are not restricted to the exact order shown, and, in other configurations, shown steps may be omitted or other intermediate steps added.

When the wearer encounters a piece of information they want to remember but think they are at risk of forgetting (the starting step 300), they simply press the single button on the device (step 302) to initiate a schedule of vibrational or tactile reminders.

Examples of situations where a user may push the button include:
A. upon learning the name of someone they were just introduced to;
B. upon another person in a conversation mentioning the name of a company or organization they want to remember;
C. upon hearing phone numbers or addresses
D. upon creating a password;
E. when thinking of tasks that they need to remember to complete in the future.

In response to receiving a signal from the button that the button has been pressed, the microcontroller initiates a series of tactile reminders (e.g., vibrations driven by the vibration motor) that come at increasingly long intervals (step 304).

The tactile reminders are perceived by the wearer of the device and each reminds the wearer to consciously and proactively remember the piece of information. The tactile reminders can be thought of as refresh signals being sent to the user by the wearable device instructing the user to reaffirm (i.e., make another effort to think about and remember) the piece of information that was important to the user. At first the reminders come more quickly to help the user make sure the piece of information does not slip away from mind. Over time, the microprocessor increasingly spaces out the reminders from one another as the piece of information becomes more affirmed in the user's memory.

When the wearer is confident that they remember the piece of information (or have had the chance to write it down), they simply terminate the reminder schedule on the device by long-press of the same button (step 306). LED indicators show the progress of the reminders schedule. On the other hand, if the user does not terminate the schedule, after a certain point, the microcontroller ends the schedule after the last tactile reminder (step 308).

As shown, the device may be considered to be in one of two modes at any given time: a ready state (step 310) where the microprocessor is waiting for the user to press the button in order to initiate a sequence of tactile reminders, and another state comprising step 303 where the processors is actually generating the sequence of increasingly spaced out tactile reminders while waiting for either the sequence to either naturally end or for the user to manual abort the sequence.

Figure 6:
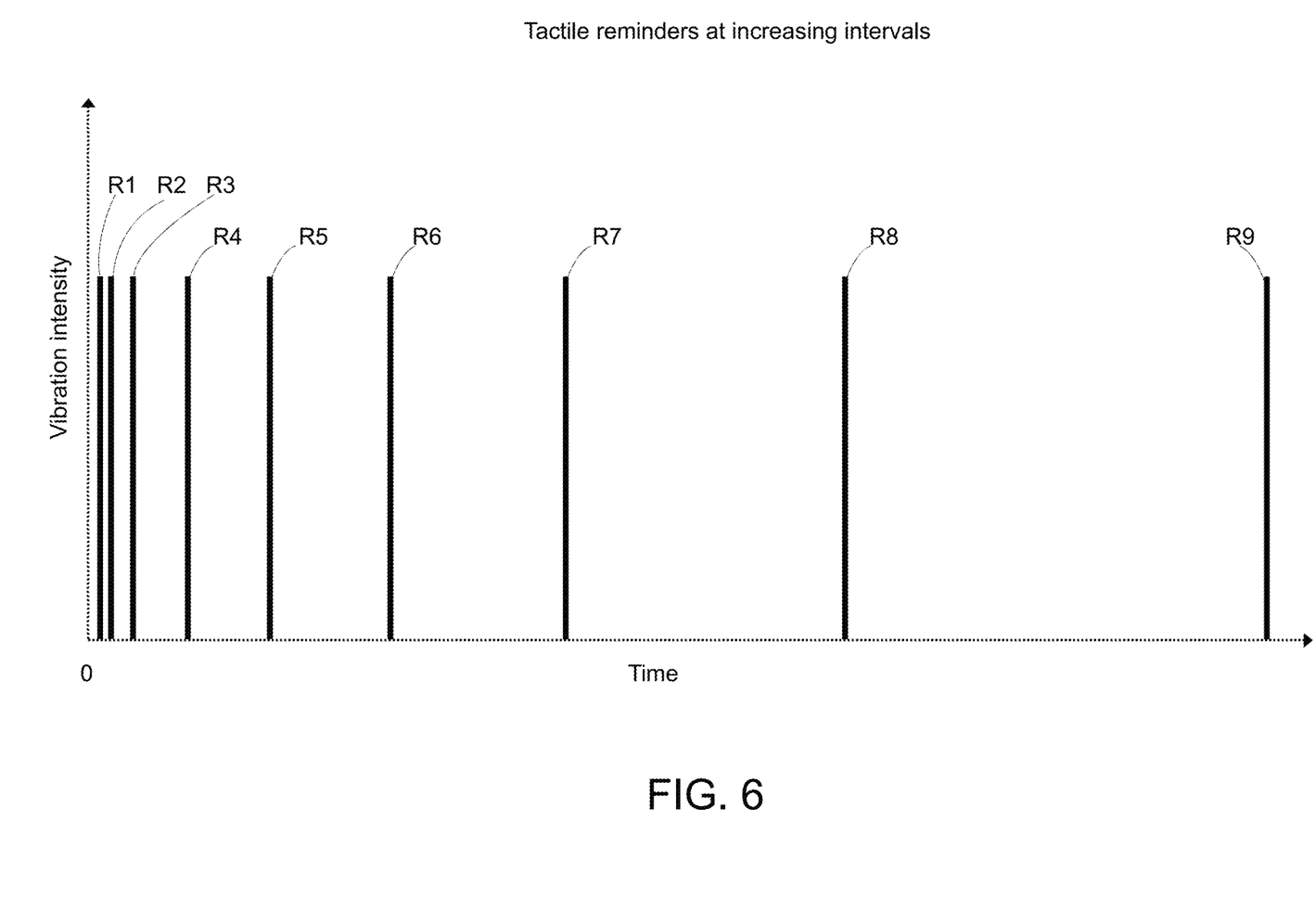
FIG. 6 illustrates a timeline diagram illustrating an exemplary sequence of tactile reminders that may be generated by the microcontroller at step 304 of FIG. 5.

FIG. 6 illustrates a timeline diagram illustrating an exemplary sequence of tactile reminders that may be generated by the microcontroller at step 304. For example, each tactile remember may be formed by a 1-5 second in duration vibration, and the tactile reminders may occur in a sequence as follows:

R1—5 seconds after button originally pressed at step 302
R2—10 seconds after button originally pressed at step 302
R3—30 seconds after button originally pressed at step 302
R4—60 seconds (1 minute) after button originally pressed at step 302
R5—120 seconds (2 minutes) after button originally pressed at step 302
R6—240 seconds (4 minutes) after button originally pressed at step 302
R7—480 seconds (8 minutes) after button originally pressed at step 302
R8—960 seconds (16 minutes) after button originally pressed at step 302
R9—1920 seconds (32 minutes) after button originally pressed at step 302

The sequence of tactile reminders may continue in this exponentially increasing manner until a last reminder occurs some period of time approximately eight hours after the original button press.

Beneficially, the reminder schedule can be initiated by the wearer without others noticing, and without resorting to the much more cumbersome and intrusive memory augmentation techniques discussed above. Advantages of wearing and utilizing the device include improving overall memory performance and confidence in memory ability, particularly amongst those who are worried about the normative declines in memory that typically accompany the aging process.

The logic of the device and in particular of the schedule of vibrational reminders is based on an empirically supported memory strategy called 'spaced retrieval'. Although spaced retrieval is well-known to be effective, it is not easily implemented by normal people. The problem is, if you can remember to do the spaced retrieval intervals, then you very likely did not need the strategy in the first place. On the other hand, if you cannot remember to do the spaced retrieval intervals, you are not going to remember what you wanted to remember.

The wearable device may be a "memory on hand"™ memory assistance device being a standalone and discrete device having benefits in certain situations when compared to a phone app that could be created with similar functionality. Two primary benefits of the standalone and dedicated nature of the device include: a) the people who may benefit most from this technology (i.e. healthy aging adults) are not predisposed to use smartphones and apps; and b) phones still impose too much 'friction' to be implemented in the way the above-described wearable device can be used. Users would have to wake their phones, enter their password, open the app, and only then initiate the reminder schedule. For these reasons, the standalone device of this embodiment with dedicated functionality accessible at the press of a single button is much more suited as a realistic option for memory augmentation in real life. Beneficially, when in the ready state (step 310), a user can initiate the sequence of reminders at any time by pressing the button—there is no requirement for the user to take other actions to otherwise wake up or unlock the wearable device.

Although the device is simple, a significant benefit is achieved by the simple structure and technical functioning of the device thereby removing the friction between wanting to remember something, and having the ability to direct the user's attention back to it in the future.

Although the invention has been described in connection with preferred embodiments, it should be understood that various modifications, additions and alterations may be made to the invention by one skilled in the art without departing from the spirit and scope of the invention. For example, although the simplicity of the above-disclosed embodiment is particularly suitable for senior citizens and those with existing memory decline, additional options and features may be included in other embodiments.

In some embodiments, the device utilizes a reversible band with a different colour on the inside to aid with 'prospective memory' i.e., remembering to do things in the future. If, for example, the user wants to remember to pick up milk on the way home from work, they can flip the band inside-out (exposing a bright colour) as a visual reminder to do so.

In some embodiments, the device utilizes rechargeable batteries instead of a coin cell battery, with charging port or wireless charging capabilities.

In some embodiments, the device is mechanically powered, with energy gained from user movement rather than battery power, and tactile reminders being generated by mechanical watch design rather than a programmable circuit board controller.

In some embodiments, the device incorporates a screen instead of LED indicators to illustrate progression through the schedule of tactile reminders.

In some embodiments, a similar device in the form of a ring is utilized, rather than a bracelet.

In some embodiments, the device utilizes a Bluetooth connection to a dedicated smartphone app, allowing a greater degree of control over the specific timings of the reminder schedule.

In some embodiments, the device is manufactured as a small component that attaches to an existing watch or other accessary of the user, rather than incorporating a separate bracelet.

In some embodiments, the device is implanted subcutaneously rather than worn on a bracelet or band.

In some embodiments, the device band tightens slightly as a tactile reminder rather than or in addition to a vibration or haptic alert.

In some embodiments, the device utilizes mild electric shocks as a reminder rather than or in addition to a vibration or haptic alert.

In some embodiments, the device utilizes a schedule of reminders decreasing in interval duration rather than increasing. In this case, a future date and/or time could be set, and reminders would come closer together as that time approaches.

In some embodiments, the device incorporates an on/off switch.

Although the above description has focused on a standalone, dedicated wearable device, in other embodiments, the device or functionality described herein may also be integrated with or added to other devices. For instance, a mobile phone could be modified or designed to include a dedicated button (or reprogrammed by a custom software application to modify an existing button such as the power or mode button) to act as the push button switch of a memory assistance device acting similar to as described above for the wearable device. A software application may be kept running and active in the background such that, at any time the button is pressed, the processors of the mobile phone will initiate the sequence of increasingly spaced tactile reminders—even when the button is pressed while the mobile phone is locked or sleeping. The tactile reminders may utilize the existing vibration motor of the mobile phone. Similar software and/or hardware modifications may also be done on other electronic and computerized devices such as tablets or netbooks such that these devices may act as a memory assistance device in addition to their regular functionality.

1. A wearable device comprising: (A) a processor; (B) at least one haptic output device coupled to the processor; (C) a specific but programmable vibrational and/or haptic feedback reminder schedule that is initiated by the user; (i) wherein the reminder schedule consists of a series of reminders that become more and more 'spaced-out' over time—e.g. immediately→5 s→10 s→30 s→1 m→3 m→5 m etc. up to perhaps 6-10 hours (may be a user configurable setting).
2. The wearable device of clause 1, wherein the reminder schedule can be altered by the user—i.e. the reminders can be 'pushed' closer together for those having more difficulty with memory or further apart for those better able to remember.
3. The wearable device of clause 2, wherein the alteration of the reminder schedule is done by some kind of easy/medium/hard toggle switch, or by different versions of the product in easy/medium/hard varieties.
4. The wearable device of clause 1, further comprising an on/off button coupled to the processor for user initiation and cancellation of specific haptic reminder schedules.
5. The wearable device of clause 1, further comprising an affixing element to physically and temporarily attach the device to the user.
6. The wearable device of clause 1, wherein the device is toggled between actively executing specific tactile or haptic feedback reminder schedules, or in a passive standby mode awaiting user initiation.
7. The wearable device of clause 1, wherein the band comprises a loop sized to fit over a user's wrist.
8. The wearable device of clause 1, wherein the device is attached to an existing wearable device or article of clothing.
9. The wearable device of clause 1, wherein the band comprises a flexible elastomeric material.
10. The wearable device of clause 1, wherein the haptic output is an output device selected from a group of devices consisting of a vibration device, a heating element, a cooling element, an electroreactive polymer, a capacitor-type voltage source, and a Braille actuator.

11. A method of utilizing the wearable device of clause 1, the method comprising, when the wearer of the device encounters a piece of information they want to remember but thinks they may forget (e.g. the name of someone they just met; a phone number; a coupon code; an address; a new word definition; anything that you might consider jotting down on a notepad if it were immediately available without any social or logistical 'friction') they simply press the single button on the device. The single button press initiates a pre-set schedule of haptic reminders about that piece of information. The reminders come quickly at first, and then become more spaced out over time. In doing so, the device is essentially a physical/electronic aid to the empirically supported memory strategy of 'spaced retrieval'—which is quite effective, but difficult to implement in practice.

12. The method of clause 11, wherein the utility of the schedule of haptic feedback reminders is iteratively utilized to maximize user memory consolidation and retrieval.

The above-described functionality of the flowchart may be performed by one or more processors included in a central processor unit (CPU) of a microcontroller or other computing device acting as the microcontroller. In this description the plural form of the word "processors" is utilized as it is common for a CPU of a computer or embedded device to have multiple processors (sometimes also referred to as cores); however, it is to be understood that a single processor may also be configured to perform the described functionality in other implementations.

The above-described functionality may be implemented as software executed by one or more processors operating pursuant to instructions stored on a tangible computer-readable medium such as a storage device to perform the above-described functions of any or all aspects of the microcontroller. Examples of the tangible computer-readable medium include optical media (e.g., CD-ROM, DVD discs), magnetic media (e.g., hard drives, diskettes), and other electronically readable media such as flash storage devices and memory devices (e.g., RAM, ROM). The computer-readable medium may be local to the computer executing the instructions, or may be remote to this computer such as when coupled to the computer via a computer network such as the Internet. The processors may be included in a general-purpose or specific-purpose computer that becomes the microcontroller or any of the above-described modules as a result of executing the instructions.

In other embodiments, rather than being software modules executed by one or more processors, the above-described functionality of the microcontroller may be implemented as hardware modules configured to perform the above-described functions. Examples of hardware modules include combinations of logic gates, integrated circuits, field programmable gate arrays, and application specific integrated circuits, and other analog and digital circuit designs.

Functions of single units may be separated into multiple units, or the functions of multiple modules may be combined into a single unit. Unless otherwise specified, features described may be implemented in hardware or software according to different design requirements. All combinations and permutations of the above-described features and embodiments may be utilized in conjunction with the invention.

What is claimed is:

1. A wearable device for assisting a wearer to remember a piece of information encountered by the wearer, the wearable device comprising:
a processor;
at least one output device coupled to the processor; and
a storage device coupled to the processor;
wherein the storage device stores therein a plurality of software instructions; and
by executing the plurality of software instructions loaded from the storage device, the processor is configured to:
wait to receive a signal indicating that the wearer has encountered the piece of information that the wearer wishes to remember;
in response to receiving the signal, initiate generation of a sequence of reminders utilizing the at least one output device, each of the reminders in the sequence being a duration of output by the at least one output device for being perceived by the wearer and thereby reminding the wearer to make another effort to think about and remember the piece of information; and
temporally space apart each of the reminders in the sequence from one another over time in an increasing manner such that the reminders occur less frequently in the sequence as time goes forward, wherein a first time duration between a particular reminder and a prior reminder in the sequence is shorter than a second time duration between the particular reminder and a subsequent reminder in the sequence.

2. The wearable device of claim 1, wherein:
the sequence of reminders are generated by the processor according to a reminder schedule stored in the storage device; and
the reminder schedule is configurable by the wearer such that the reminders in the sequence may be generated to occur closer to one another in time while still being temporally spaced apart in time in the increasing manner when the wearer is having more difficulty remembering desired information, and such that the reminders in the sequence may be generated to occur further apart from one another in time while still being temporally spaced apart in time in the increasing manner when the wearer is having less difficulty remembering desired information.

3. The wearable device of claim 2, further comprising:
a toggle switch coupled to the processor;
wherein the reminder schedule is configurable by the wearer changing a position of the toggle switch.

4. The wearable device of claim 1, further comprising a band forming a loop sized to fit over a wrist of the wearer.

5. The wearable device of claim 1, wherein the wearable device is worn by the wearer attaching the wearable device to an existing wearable device or to an article of clothing of the wearer.

6. The wearable device of claim 1, wherein the at least one output device is selected from a group of devices consisting of a vibration device, a heating element, a cooling element, an electroreactive polymer, a capacitor-type voltage source, an LED indicator, and a Braille actuator.

7. The wearable device of claim 1, further comprising:
a button coupled to the processor;
wherein the signal indicating that the wearer has encountered the piece of information that the wearer wishes to remember is generated by the button upon the button being pressed by the wearer.

8. A method of utilizing the wearable device of claim 7, the method comprising:
when the wearer of the wearable device encounters the piece of information the wearer wants to remember, the wearer presses the button on the wearable device;
the processor receives the signal from the button and in response initiates generation of the sequence of reminders;
the reminders in the sequence are generated by the processor utilizing the at least one output device and are temporally spaced out in time in the increasing manner, wherein due to the reminders in the sequence being temporally spaced out by the processor in the increasing manner, the reminders come more quickly at first in the sequence and then become more separated from one another in time as the sequence of reminders progresses; and
each time a reminder in the sequence in generated by the at least one output device of the wearable device, the wearer perceives the reminder and makes another effort to think about and remember the piece of information, thereby reaffirming the piece of information in the wearer's mind.

9. The wearable device of claim 7, wherein, after initiating generation of the sequence of reminders, the processor is further configured to cancel generation of the sequence of reminders in response to a second press of the button.

10. The wearable device of claim 9, wherein the processor only cancels generation of the sequence of reminders in response to the second press of the button when the second press of the button is of a predetermined long-press duration.

11. The method of claim 8, further comprising:
when the wearer is confident that the wearer remembers the piece of information or decides that the wearer no longer needs to remember the piece of information such as because the wearer has had a chance to write down the piece of information, the wearer does a second press of the button; and
the processor detects the second press of the button and terminates generation of the sequence of reminders.

12. The wearable device of claim 1, wherein:
the at least one output device is a haptic output device; and
each of the reminders in the sequence is a tactile reminder generated by the haptic output device.

13. The wearable device of claim 1, wherein the processor is configured to temporally space apart each of the reminders in the sequence from one another over time in an exponentially increasing manner.

14. The wearable device of claim 1, wherein:
the sequence of reminders includes a predetermined number of reminders; and
the processor is configured to terminate the sequence of reminders after generating a last reminder of the sequence.

15. The wearable device of claim 1, wherein the processor is configured to terminate the sequence of reminders after a predetermined amount of time has passed since receiving the signal.

16. The wearable device of claim 1, wherein:
after terminating the sequence of reminders, the processor is further configured to begin waiting for a next signal indicating that the wearer has encountered a next piece of information that the wearer wishes to remember; and
in response to receiving the next signal, initiate another generation of the sequence of reminders utilizing the at least one output device.

17. The wearable device of claim 1, wherein the processor is configured to temporally space apart each of the reminders in the sequence from one another over time in the increasing manner such that:
a first reminder is generated immediately after receiving the signal;
a second reminder is generated 5 seconds after receiving the signal;
a third reminder is generated 10 seconds after receiving the signal;
a fourth reminder is generated 30 seconds after receiving the signal;
a fifth reminder is generated 1 minute after receiving the signal;
a sixth reminder is generated 3 minutes after receiving the signal; and
a seventh reminder is generated 5 minutes after receiving the signal.

18. The wearable device of claim 1, wherein the processor is configured to temporally space apart each of the reminders in the sequence from one another over time in the increasing manner such that:
a first reminder is generated 5 seconds after receiving the signal;
a second reminder is generated 10 seconds after receiving the signal;
a third reminder is generated 30 seconds after receiving the signal;
a fourth reminder is generated 60 seconds after receiving the signal;
a fifth reminder is generated 120 seconds after receiving the signal;
a sixth reminder is generated 240 seconds after receiving the signal;
a seventh reminder is generated 480 seconds after receiving the signal;
an eighth reminder is generated 960 seconds after receiving the signal; and
a ninth reminder is generated 1920 seconds after receiving the signal.

19. A method performed by a wearable device for assisting a wearer of the wearable device to remember a piece of information encountered by the wearer, the method comprising:
waiting to receive a signal indicating that the wearer has encountered the piece of information that the wearer wishes to remember;
in response to receiving the signal, initiating generation of a sequence of reminders utilizing at least one output device of the wearable device, each of the reminders in the sequence being a duration of output by the at least one output device for being perceived by the wearer and thereby reminding the wearer to make another effort to think about and remember the piece of information; and
temporally spacing apart each of the reminders in the sequence from one another over time in an increasing manner such that the reminders occur less frequently in the sequence as time goes forward, wherein a first time duration between a particular reminder and a prior reminder in the sequence is shorter than a second time duration between the particular reminder and a subsequent reminder in the sequence.

20. A non-transitory processor-readable medium comprising processor executable instructions that when executed by one or more processors of a wearable device cause the one or more processors to perform a method for assisting a wearer of the wearable device to remember a piece of information encountered by the wearer, the method comprising:
- waiting to receive a signal indicating that the wearer has encountered the piece of information that the wearer wishes to remember;
- in response to receiving the signal, initiating generation of a sequence of reminders utilizing at least one output device of the wearable device, each of the reminders in the sequence being a duration of output by the at least one output device for being perceived by the wearer and thereby reminding the wearer to make another effort to think about and remember the piece of information; and
- temporally spacing apart each of the reminders in the sequence from one another over time in an increasing manner such that the reminders occur less frequently in the sequence as time goes forward, wherein a first time duration between a particular reminder and a prior reminder in the sequence is shorter than a second time duration between the particular reminder and a subsequent reminder in the sequence.

* * * * *